Figure 1:
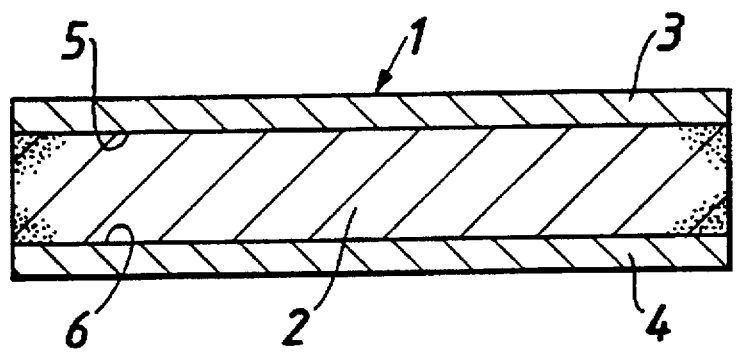

United States Patent [19]
Penrose

[11] Patent Number: 5,718,674
[45] Date of Patent: Feb. 17, 1998

[54] BANDAGES

[75] Inventor: Jane Edith Penrose, Skipton, United Kingdom

[73] Assignee: Smith & Nephew plc, London, United Kingdom

[21] Appl. No.: 635,903

[22] PCT Filed: Nov. 4, 1994

[86] PCT No.: PCT/GB94/02432

§ 371 Date: May 3, 1996

§ 102(e) Date: May 3, 1996

[87] PCT Pub. No.: WO95/12375

PCT Pub. Date: May 11, 1995

[30] Foreign Application Priority Data

Nov. 4, 1993 [GB] United Kingdom ............. 9322711
Nov. 4, 1993 [GB] United Kingdom ............. 9322715
Nov. 4, 1993 [GB] United Kingdom ............. 9322717

[51] Int. Cl.$^6$ ........................................ A61F 5/00
[52] U.S. Cl. .................. 602/46; 602/54; 602/75; 602/77
[58] Field of Search .................. 602/41, 42, 43, 602/44, 45, 46, 47, 52, 53, 54, 55, 56, 75, 76, 77; 128/888, 889, 892, 893, 894

[56] References Cited

U.S. PATENT DOCUMENTS 4,146,027  3/1979  Hoey.

FOREIGN PATENT DOCUMENTS 1320628  6/1973  United Kingdom.
8607533  12/1986  WIPO.

*Primary Examiner*—Richard J. Apley
*Assistant Examiner*—Kim M. Lee
*Attorney, Agent, or Firm*—Larson & Taylor

[57] ABSTRACT

There are described bandages which comprise a cohesive coated open cellular polymeric foam material which has a cellular surface area, at least 15% of the total surface area of the surface of the bandages comprise open cells of said open cellular polymeric foam material.

17 Claims, 1 Drawing Sheet

BANDAGES

This invention relates to a novel form of bandages and methods for their manufacture.

Cohesive retention bandages are known such as those sold by Smith & Nephew Medical Limited under the name EASIFIX Cohesive in the UK. Although such bandages are relatively easy to apply they are difficult to tear and therefore must be cut to the appropriate length with scissors. Tearable bandages are known but generally they are not sufficiently cohesive to act as cohesive retention bandages.

Cohesive bandages are also known from British Patent No. 1320628 which describes a cohesive sheet comprising a porous, resilient open cellular web having a cell density of from 10 to 120 cells per inch and the cellular surface occupying less than 15% of the total area of the web when the web is in a non-compressed state. GB '628 suggests that webs with a cellular surface occupying greater than 15% of the total area of the web will have unsatisfactory unwind characteristics.

We have now surprisingly found that by coating certain open cellular polymeric foams with a cohesive coating these problems can be overcome or mitigated.

According to the invention we provide a bandage comprising an open cellular polymeric foam material provided with a cohesive coating characterized in that the cellular surface area on the bandage comprises at least 15% of the total surface area when the bandage is non-compressed.

The polymeric foam material may comprise a sheet or strip of material. Alternatively, the foam may be in the form of a net which net comprises a layer of foam provided with apertures or slits. The cohesive coating may be provided on only one side of the foam material, alternatively greater cohesion is achieved if the cohesive coating is on both sides of the foam material.

The cohesive coating may be a continuous layer although a non-continuous layer of cohesive coating is preferred.

Any conventionally known cohesive coatings may be used including synthetic cohesive materials. Preferred cohesive materials are rubbers which may be applied as a latex coating. The cohesive material is usually coated onto the material at a density of 5 to 20 g m$^{-2}$ for one side of the material, preferably 5 to 15 g m$^{-2}$ and especially 8 to 15 g m$^{-2}$.

Any conventional open cell polymeric foam material may be used, foams which possess elastomeric properties are preferred. The latex coating will tend to render even hydrophilic foams as hydrophobic, but generally hydrophobic foams are preferred. It is within the scope of this invention to include profiled or reticulated foams.

The surface area of the open cells on the bandage may be from 15 to 70% of the total surface area when the bandage is non-compressed, preferably from 30 to 70%, more preferably from 40 to 70% and especially from 50 to 70% of the total surface area when the bandage is non-compressed.

The size of the open cells may be from 0.3 to 1.0 mm, preferably from 0.4 to 0.9 mm and more preferably from 0.4 to 0.8 mm.

The cellular surface area and the open cell size may be determined by Scanning Electron Microscopy (SEM).

Preferred foams are polyester foams and especially polyester/polyurethane foams. Foams with a high cellular area as hereinbefore described are also preferred. Such foams are commercially available from Caligen of Accrington in the United Kingdom.

Although polyester and polyester/polyurethane foams are known such foams have not been used as bandages. Thus according to a further feature of the invention we provide the use of a polyester or a polyester/polyurethane foam in the manufacture of a bandage. In particular we provide the use of a cohesive coated, eg. rubber coated polyester or polyester/polyurethane foam in the manufacture of a bandage.

Polyester and polyester/polyurethane foams are advantageous since they possess properties which render the material particularly suitable as a bandage. Bandages of the invention and polyester or polyester/polyurethane foam bandages in particular are "cross-tearable". Conventional fabric bandages must be cut, eg. using scissors, which can be cumbersome. Whereas bandages of the invention can be torn by hand to produce a bandage of appropriate length.

Thus according to the invention we provide a cross-tearable bandage which bandage comprises a polymeric foam material, eg. an open cellular polymeric foam material as hereinbefore described. Polyester or polyester/polyurethane foams are preferred and particularly cohesive coated foams as hereinbefore described.

The tear strength of bandages according to the invention may be from 100 to 700 gf, preferably from 100 to 500 gf, more preferably from 200 to 300 gf, eg. 240 gf.

When used as a bandaging material the foam may have a thickness of from 1.0 to 6.0 mm, eg. about 3.0 mm.

The foam according to the invention may also have a density of from 28 to 32 kg m$^{-3}$.

The foam may also have a tensile strength of at least 160 kPa and an elongation at break of at least 250%.

Coarse, medium or fine foams may be used. A fine foam is generally a foam with a cell count of greater than 17 per cm$^3$, a medium foam generally has a cell count of from 13 to 19 per cm$^3$ and a coarse foam generally has a cell count of less than 13 cells per cm$^3$.

The foam may have a hardness of from 140 to 200 N and a compression set of not greater than 10%.

The bandages of the invention are particularly useful as retention bandages. Thus according to the invention we provide a method of retaining a dressing and body portion which comprises applying a dressing to said body portion and wrapping a bandage according to the invention around the body portion and over the dressing and fixing the ends of the bandage to the wrapped bandage.

By the term bandages we mean conventionally known bandages, such as retention or compression bandages. However, the term bandages is also intended to incorporate padding materials, such as those used underneath orthopaedic casts. Materials with a high cellular surface area have the advantage of being "cross-tearable" as hereinbefore described, but are also, when rubber coated, such materials will be hydrophobic.

Padding materials for placing beneath an orthopaedic casting usually comprise soft conformable materials such as natural or synthetic non-woven materials, e.g. those sold by Smith & Nephew Medical in the U.K. under the name SOFFBAN.

However, such materials suffer from the disadvantage that they are generally unsuitable for use with water hardenable resin orthopaedic casts. Moreover, once such resin casts are set they can be brought into contact with water without any deterioration occurring, thus giving the patient much more freedom to carry on a normal life. However, since the underpadding absorbs water and generally suffers damage to its structure when in contact with water this limits the patient's freedom.

Thus according to the invention we provide an undercast padding material comprising an open cellular polymeric foam material which foam is provided with a cohesive coating characterised in that the cellular surface area on the bandage comprises at least 15% of the total area when the bandage is non-compressed.

When used as an orthopaedic undercast padding material the foam may have a thickness of from 4.0 to 6.0 mm, eg. 5.0 mm.

According to the invention we provide a method of treatment of fracture of a body portion which comprises applying a layer of the foam according to the invention followed by applying a hardenable casting material.

The method is particularly advantageous in that where the casting material is a water hardenable material, eg. a resin, the body portion dressed in the underpadding and the hardenable casting material may be immersed in water. Thus we provide a method of treatment as hereinbefore described wherein the body portion is immersed in water.

According to a further feature of the invention we provide a kit comprising an undercast padding material as hereinbefore described and an orthopaedic casting tape, eg. a resin coating casting tape such as a water hardenable resin coated casting tape.

The bandage according to the invention may be manufactured by conventional methods known per se, but preferably the cohesive coating is sprayed onto the polymeric foam material. The resulting coated material is then dried.

According to the invention we therefore provide a method of manufacturing a bandage as hereinbefore described which comprises coating a polymeric foam with a layer of a cohesive material and then drying the product, eg. in an infra red drying tower.

Figure 2:
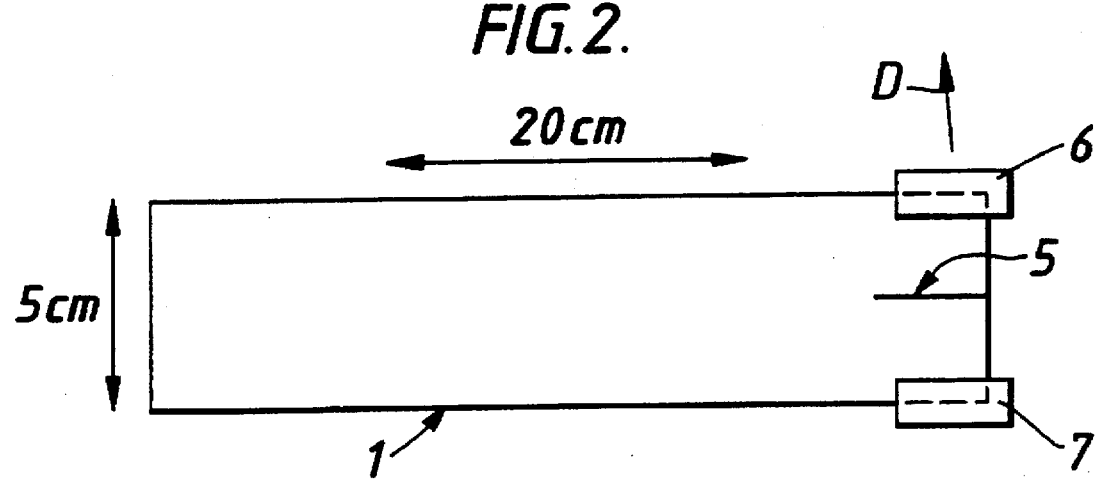

The invention will now be described, but in no way limited by reference to the accompanying drawing in which FIG. 1 is a cross-section of a cross-tearable bandage according to the invention, and FIG. 2 is a schematic representation of a bandage of the invention undergoing a tear test.

With reference to FIG. 1, the bandage (1) comprises a foam layer (2) and latex layers (3 and 4) on opposing faces (5 and 6) of the foam layer. The latex layers (3 and 4) may be non-continuous (not shown).

With reference to FIG. 2, the bandage (1) comprises a slit (5) and is attached to jaws (6 and 7). Jaw (7) remains fixed while jaw (6) is moved in a direction (D) to cause tearing of the bandage along the slit.

The invention will now be illustrated but in no way limited by the following Examples.

EXAMPLE 1

Bandages were prepared from pigmented polyester/polyurethane foam manufactured by Caligen Foam Ltd. The material was supplied in reel form at the required width (10 cm) and thickness. The foam was spray coated on both sides with a natural rubber latex emulsion at a coating weight of 7–25 g m$^{-2}$. The applied weight was varied to obtain 'usable' samples. The rubber latex was supplied by EVODE, referenced Tivotex 2057/5 which is a water based, natural rubber latex emulsion at about 60% solids content. The bandages were spooled automatically after drying onto cardboard cones. These were tested for;

ThomasTest Type 1 (Retention)
Unrolling tension
Tear strength
Cohesive strength

EXAMPLE 2

A bandage was prepared using the same polyester/polyurethane and the same method as Example 1.

A foam of 1.0 mm thickness was used and a coating weight of 10 g m$^{-2}$ of rubber latex was applied.

EXAMPLE 3

Uncoated and latex coated polyester/polyurethane foams were subjected to physical tests using conventional methods known per se. The test results are shown in Tables I and II.

EXAMPLE 4

Tear Strength

Tear Strength testing was performed using the following method, on latex coated material of varying thicknesses.

A sample of the bandage, of approximate dimensions 20 cm×5 cm with a slit of approximately 2 cm cut in the top of the sample (see FIG. 2) was placed within the jaws (D) of an Instron tensile testing instrument. The jaws of the Instron are moved apart at a speed of 300 mm/min and the load required is measured. The results are quoted as an average of 3 individual results.

TABLE III

| Thickness (mm) | Tear Strength (gf) |
| --- | --- |
| 1.75 | 570 |
| 1.75 | 645 |
| 1.50 | 320 |
| 1.25 | 380 |
| 1.00 | 240 |
| 0.75 | 155 |

TABLE I

| | | | Polyester Foam Physical Test Results (Uncoated) | | | | | |
| --- | --- | --- | --- | --- | --- | --- | --- | --- |
| Thickness (mm) | Elongation At Break (%) | Tensile Strength (Kgfcm-1) | Type 1 Extension (%) | Type 1 Factor (%) | Type 1 Tension Ratio (%) | Type 3a Extension (%) | Type 3a Factor (%) | Type 3a Tension Ratio (%) |
| 0.75 | 341 | 0.13 | 39.6 | 2.60 | 75.7 | 154.3 | 3.24 | 81.8 |
| 1.00 | 326 | 0.15 | 41.2 | 2.57 | 73.6 | 129.3 | 3.32 | 81.3 |
| 1.25 | 321 | 0.29 | 14.3 | 2.23 | 61.2 | 43.7 | 3.46 | 78.6 |
| 1.50 | 358 | 0.30 | 23.8 | 2.43 | 69.5 | 67.6 | 3.57 | 80.4 |

TABLE II 1.75 mm Thick Polyester Foam Physical Test Results (Coated)

| Unrolling Tension (gfcn-1) | Cohesive Strength (gfcm-1) | Elongation At Break (%) | Tensile Strength (Kgfcm-1) | Type 1 Extension (%) | Type 1 Factor (%) | Type 1 Tension Ratio (%) | Type 3a Extension (%) | Type 3a Factor (%) | Type 3a Tension Ratio (%) |
| --- | --- | --- | --- | --- | --- | --- | --- | --- | --- |
| 90.0 | 31.0 | 351 | 0.37 | 11.0 | 1.45 | 52.9 | 31.1 | 2.97 | 755 |
| 200.0 | 63.0 | 352 | 0.43 | 14.7 | 3.77 | 60.6 | 32.0 | 3.77 | 80.0 |

I claim:

1. A cross-tearable bandage comprising a web of open cellular polymeric foam material having a surface, said open cellular polymeric material being provided with a cohesive coating, at least 15% of the total surface area of said surface of said open cellular web comprising open cells of said polymeric foam material when the bandage is non-compressed.

2. A bandage according to claim 1 wherein from 15 to 70% of the total surface area of said surface of said web comprises open cells of said open cellular polymeric foam material when the bandage is non-compressed.

3. A bandage according to claim 1 wherein the cohesive coating comprises rubber.

4. A bandage according to claim 1 wherein the cohesive coating is applied at a coating weight of from 5 to 20 g m$^{-2}$.

5. A bandage according to claim 1 which has a tear strength of from 100 to 700 gf.

6. A bandage according to claim 1 wherein said polymeric foam material comprises a polyester.

7. A bandage according to claim 1 wherein from 30 to 70% of the total surface area of said surface of said web comprises open cells of said open cellular polymeric foam material when the bandage is non-compressed.

8. A bandage according to claim 1 wherein from 40 to 70% of the total surface area of said surface of said web comprises open cells of said open cellular polymeric foam material when the bandage is non-compressed.

9. A bandage according to claim 1 wherein from 50 to 70% of the total surface area of said surface of said web comprises open cells of said open cellular polymeric foam material when the bandage is non-compressed.

10. A method of retaining a dressing which comprises applying a dressing to a body portion of a patient, wrapping a bandage around the body portion and over the dressing and, fixing the end of the bandage to the wrapped bandage, said bandage comprising a web of open cellular polymeric foam material having a surface, said open cellular polymeric material being provided with a cohesive coating, at least 15% of the total surface area of said surface of said web comprising open cells of said open cellular polymeric foam material when the bandage is non-compressed.

11. A method of treatment of a fracture of a body portion which comprises applying a bandage to said body portion followed by applying a hardenable cast material, said bandage comprising a web of open cellular polymeric foam material having a surface, said open cellular polymeric material being provided with a cohesive coating, at least 15% of the total surface area of said surface of said web comprising open cells of said open cellular polymeric foam material when the bandage is non-compressed.

12. A kit comprising a bandage and an orthopaedic casting tape, said bandage comprising a web of open cellular polymeric foam material having a surface, said open cellular polymeric material being provided with a cohesive coating, at least 15% of the total surface area of said surface of said web comprising open cells of said polymeric foam material when the bandage is non-compressed.

13. A method of manufacturing a bandage comprising providing a web of open cellular polymeric foam material having a surface, coating said polymeric foam web with a layer of a cohesive material, and then drying the product to provide said open cellular polymeric material with a cohesive coating, at least 15% of the total surface area of said surface of said web comprising open cells of said open cellular polymeric foam material when the bandage is non-compressed.

14. A method according to claim 13, wherein said polymeric foam material comprises a polyester.

15. A method of retaining a dressing which comprises applying a dressing to a body portion of a patient, wrapping a bandage around the body portion and over the dressing, and fixing the end of the bandage to the wrap bandage, said bandage comprising a web of open cellular polymeric foam material having a surface, said open cellular polymeric material being provided with a cohesive coating, at least 15% of the total surface area of said surface of said web comprising open cells of said open cellular polymeric foam material when the bandage is non-compressed.

16. A method of treatment of a fracture of a body portion which comprises applying a bandage to said body portion followed by applying a hardenable cast material, said bandage comprising a web of open cellular polymeric foam material having a surface, said open cellular polymeric material being provided with a cohesive coating, at least 15% of the total surface area of said surface of said web comprising open cells of said open cellular polymeric foam material when the bandage is non-compressed.

17. A kit comprising a bandage and an orthopaedic testing tape, said bandage comprising a web of open cellular polymeric foam material having a surface, said open cellular polymeric material being provided with a cohesive coating, at least 15% of the total surface area of said surface of said web comprising open cells of said open cellular polymeric foam material when the bandage is non-compressed.

* * * * *